US00PP13949P29

(12) United States Plant Patent
Stemkens

(10) Patent No.: US PP13,949 P2
(45) Date of Patent: Jul. 8, 2003

(54) DIASCIA PLANT NAMED 'DIASTU'

(75) Inventor: Henricus G. W. Stemkens, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 10/042,828

(22) Filed: Jan. 9, 2002

(51) Int. Cl.[7] ..... A01H 5/00

(52) U.S. Cl. ..... Plt./263

(58) Field of Search ..... Plt./263, 272

*Primary Examiner*—Bruce R. Campell
*Assistant Examiner*—Annette H. Para
(74) *Attorney, Agent, or Firm*—Bruce Vrana; Edouard G. Lebel

(57) ABSTRACT

A new Diascia plant particularly distinguished by its antique rose (pink) flower, early flowering and a spreading habit.

1 Drawing Sheet

LATIN NAME OF THE GENUS AND SPECIES OF THE PLANT CLAIMED

*Diascia barbarae.*

VARIETY DENOMINATION

'DIASTU'.

BACKGROUND OF THE NEW PLANT

The present invention comprises a new distinct cultivar of Diascia, botanically known as *Diascia barbarae*. The new cultivar is propagated from cuttings resulting from the cross of 'A 64-1' and 'A 65-1'. 'A 64-1' is a coral flowering Diascia having a semi-erect habit and immediate flowers. 'A 64-1' is not commercially available and is not known by any synonyms. 'A 65-1' is a lilac pink flowering Diascia having a spreading habit and small flowersize. 'A 65-1' is not commercially available and is not known by any synonyms. Neither 'A 64-1' or 'A 65-1' has been patented. As a result of this cross the present cultivar was created in 1998 in Enkhuizen, Netherlands and has been repeatedly asexually reproduced by cuttings in Enkhuizen, Netherlands and Sarrians, France over a three-year period. It has been found to retain its distinctive characteristics through successive propagations, and this novelty appears to be firmly fixed.

This new Diascia plant is an annual in most climatical zones in the U.S. Only in zones 7, 8, 9 and 10 it is a perennial plant.

DESCRIPTION OF THE DRAWING

This new Diascia plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new Diascia. The data which defines these characteristics were collected from asexual reproductions carried out in Enkhuizen, Netherlands. The plant history was taken on 10 weeks old plants, blossomed under natural light in a greenhouse. Color readings were taken in the greenhouse under ambient light. Color references are primarily to The R.H.S. Color Chart of The Royal Horticultural Society of London.

Differences between the new variety 'Diastina', its parents and a similar cultivar

| Character | 'Diastu' | 'A 64-1' | 'A 65-1" | 'Little Charmer' |
|---|---|---|---|---|
| Color | Antique Rose | Coral | Lilac Pink | Antique Rose |
| Leaf Size | Large | Large | Small | Small |
| Plant Vigor | Intermediate | Strong | Compact | Very Compact |

The Plant

Classification — botanical: *Diascia barbarae.*
Parentage:
*Female parent.*—A seedling named 'A 64-1' is one of our seedlings from our A-generation of plants bred in 1996.
*Pollen parent.*—A seedling named 'A 65-1' is one of our seedlings from our A-generation of plants bred in 1996.
Growth habit: Spreading.
Plant height: 15–22 cm.
Spreading area of plant: 20–40 cm.
Growth rate: Vigorous.
Strength: Very good.
Branching character: Freely branching and lateral branching at every node.
Quantity of branches: 130–150 branches per plant.
Blooming period: From April until November.

The Stem

Diameter: 1.0–1.5 mm.
Shape: Tetragonal.
Color: 143B.
Anthocyan pigmentation: Absent.
Length of internode:
*Vegetative growth.*—10–20 mm.
*Generative growth.*—15–35 mm.
Pubescence: Not pubescent.

The Foliage

Phyllotaxis: Opposite.
Shape of blade: Cordate to ovate.
Texture:
*Upper side.*—Smooth.
*Lower side.*—Smooth.
Attachment to leaf: Petiolate.
Venation: Pinnate.
Leaf margin: Serrate.
Leaf base: Subcordate.
Leaf apex: Acute.
Length: 20–28 mm.
Width: 16–24 mm.
Depth of incision: 1–2 mm.
Color:
*Upper side.*—Light green 141B.
*Lower side.*—Light green 147D.
Pubescence: No pubescence.
Length of petiole: 2–3 mm.
Color of petiole: Light green 141B.
Petiole surface texture: Smooth.

The Bud

Peduncle length: 20–40 mm, depending on season.
Peduncle shape: Long and threadlike.
Size:
*Diameter.*—3 mm.
*Length.*—3 mm.
Shape: Oval.
Color: Light green 141C.
Sepals:
*Color.*—Light green 141C.
*Form.*—Star-shaped.
*Number.*—5, parted.
*Size.*—1–2 mm.
*Shape.*—Elliptic, apex acute.
*Margin.*—Entire.
*Texture.*—Smooth.

The Flower

Flower width: 16–20 mm.
Flower length: 20–24 mm.
Flower depth: 10–14 mm.
Flower aspect: Tipped upward and outward.
Borne: Solitary.
Form: Zygomorphic, five lobed, double nectar spur.
Cluster: Raceme.
Color:
*Upper surface.*—Red purple N 66D.
*Lower surface.*—Red purple N 66D a shade lighter.
Overlapping of petals: Separate.
No. of petals: Five.
Shape of the petals: Two upper banner panels, two lateral petals and one larger basal lip petal. Base of two banner petals form a small yellow indentation (color yellow 5B) just above the reproductive organs. Center of two lateral petals form curved nectar spurs. Rounded lip petal is much larger and forms a bowl-like structure 'platform'.
Petal margin: Entire.
Petal surface texture: Smooth.
Size of the banner petals:
*Length.*—4–6 mm.
*Width.*—6–8 mm.
Size of the lateral petals:
*Length.*—4–6 mm.
*Width.*—7–10 mm.
Size of the basal lip petal:
*Length.*—13–15 mm.
*Width.*—13–15 mm.
Spur:
*Length.*—6 mm.
*Color.*—Greyed purple 180C towards the tips.
No. of flowers per raceme: 20–25.
Fragrance: No fragrance.
Lastingness of the bloom: New florets continue to open in one raceme over a period of 20 days.
Lastingness of one flower: About 5 days depending on temperature.

Reproductive organs

Androecium:
*Stamen number.*—3.
*Anther shape.*—Two-lobed.
*Anthur size.*—Less than 1 mm.
*Anther color.*—Yellow 9A.
*Amount of pollen.*—Very much pollen.
*Pollen color.*—Yellow 9A.
Gynoecium:
*Pistil number.*—1.
*Stigma shape.*—Rounded.
*Pistil length.*—2–3 mm.
*Style color.*—Green 144B.
*Stimas color.*—Green white 157A.
*Ovary color.*—Green 144B.

Seeds

Seedset: No seedset has been observed.

Roots

Type of roots: Fibrous.
Root description: Fine and freely branching.

Physiological and ecological characteristics

Good tolerance to heat and cold.

What is claimed is:

1. A new and distinct variety of Diascia plant, substantially as herein illustrated and described, characterized particularly as to novelty by antique rose (pink) flowers, which appear earlier on the plant, which produces no seeds, and has a growing habit that is spreading and hanging.

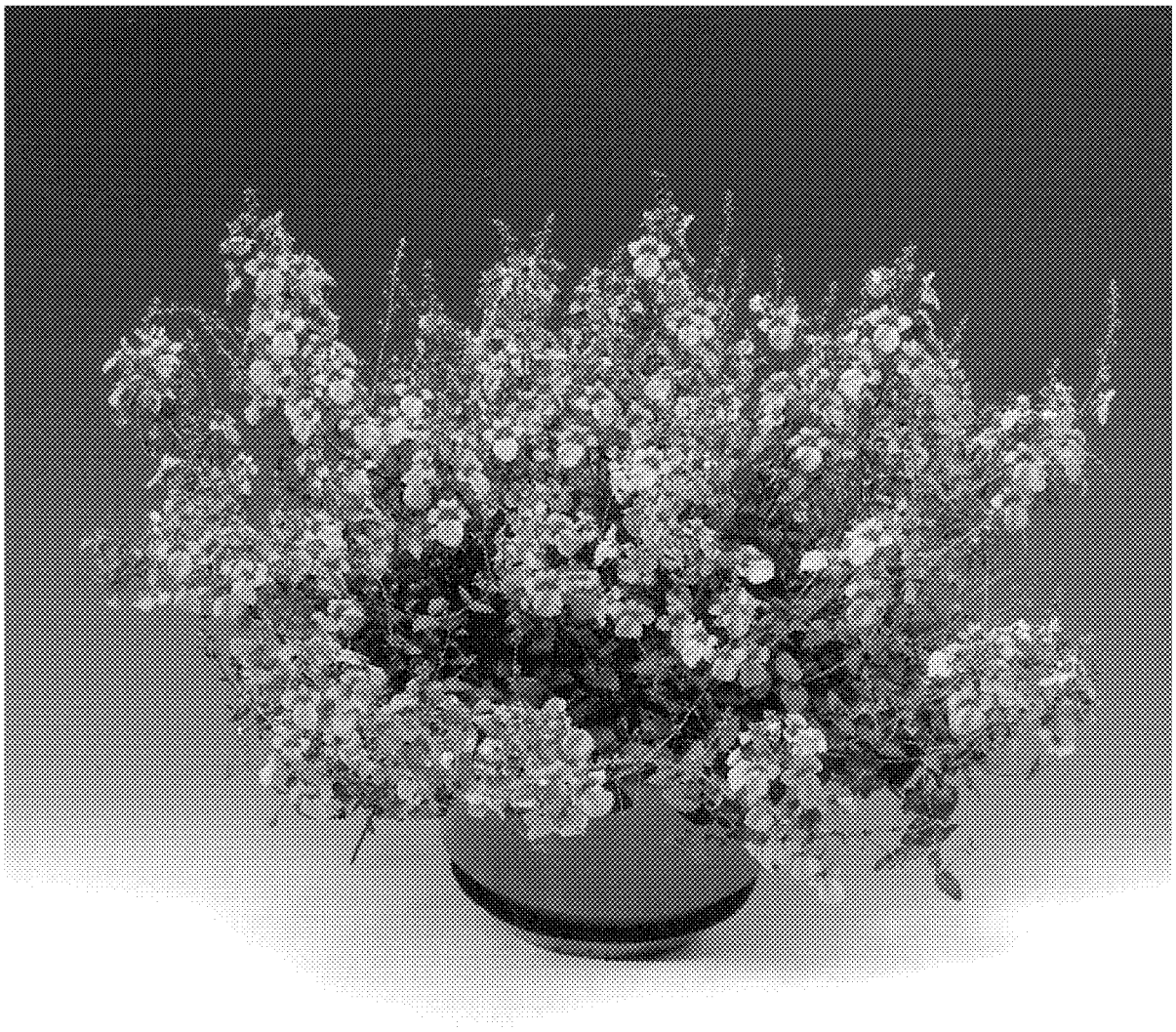

* * * * *